United States Patent [19]

Kroll et al.

[11] Patent Number: 5,507,781
[45] Date of Patent: Apr. 16, 1996

[54] IMPLANTABLE DEFIBRILLATOR SYSTEM WITH CAPACITOR SWITCHING CIRCUITRY

[75] Inventors: Mark W. Kroll, Minnetonka; Theodore P. Adams, Edina; Dennis A. Brumwell, Bloomington, all of Minn.

[73] Assignee: Angeion Corporation, Plymouth, Minn.

[21] Appl. No.: 292,354

[22] Filed: Aug. 18, 1994

Related U.S. Application Data

[63] Continuation of Ser. No. 999,393, Dec. 31, 1992, abandoned, which is a continuation-in-part of Ser. No. 704,619, May 23, 1991, Pat. No. 5,199,429.

[51] Int. Cl.[6] ............................................. A61N 1/39
[52] U.S. Cl. .................... 607/7; 607/74; 607/5
[58] Field of Search .................... 607/2, 5, 7, 15, 607/34, 37, 38, 74

[56] References Cited

U.S. PATENT DOCUMENTS

| | | | |
|---|---|---|---|
| 3,093,136 | 6/1963 | Lohr | 128/419 D |
| 3,924,641 | 12/1975 | Weiss | 607/74 |
| 4,800,883 | 1/1989 | Winstrom . | |
| 4,850,357 | 7/1989 | Bach, Jr. | 607/74 |
| 5,083,562 | 1/1992 | de Coriolis et al. | 128/419 D |
| 5,199,429 | 4/1993 | Kroll et al. | 128/419 D |
| 5,411,525 | 5/1995 | Swanson et al. | 607/5 |

FOREIGN PATENT DOCUMENTS 0272021  7/1964  Australia ........................ 128/419 D

*Primary Examiner*—William E. Kamm
*Assistant Examiner*—Kennedy J. Schaetzle
*Attorney, Agent, or Firm*—Patterson & Keough

[57] ABSTRACT

The present invention uses switches to set the topology and polarity of a circuit that includes capacitors to deliver an electric pulse to a heart during a defibrillation procedure. The waveform of the electric pulse is biphasic, in that it is a positive portion of the pulse followed by a negative portion of the pulse. The topology and polarity of the circuit are utilized to produce a waveform that approximates the ideal waveform for the specific situation. The circuit provides for combinations of capacitors variously in series and in parallel and changing the topology and polarity of the circuit during discharge of the capacitors.

7 Claims, 10 Drawing Sheets

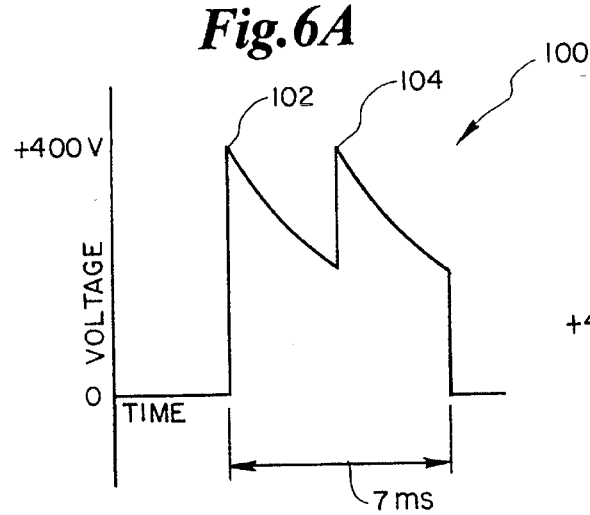
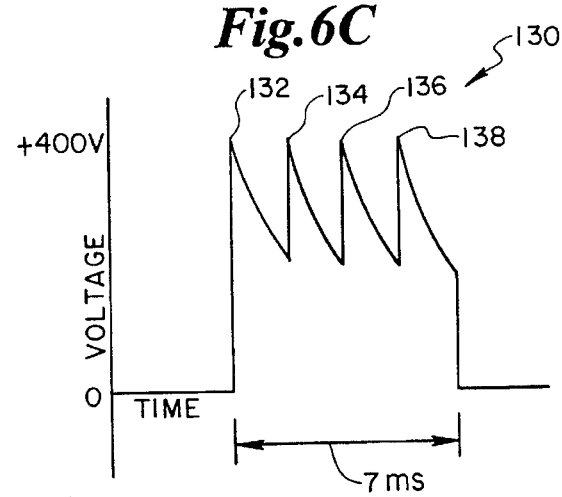
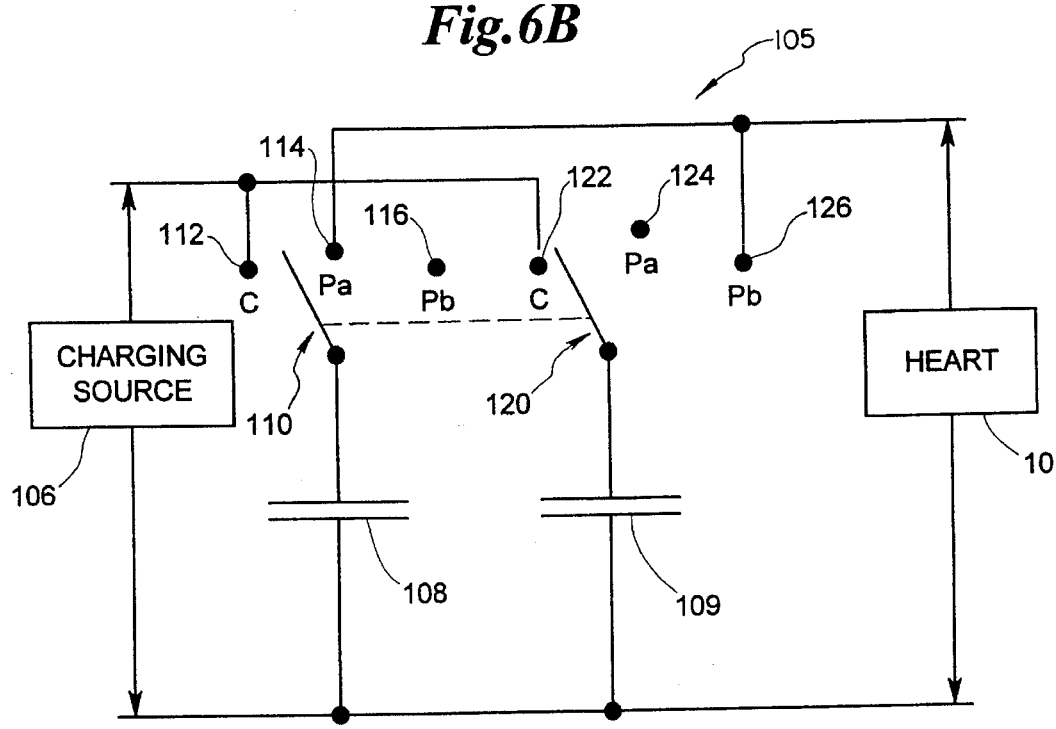

IMPLANTABLE DEFIBRILLATOR SYSTEM WITH CAPACITOR SWITCHING CIRCUITRY

CROSS REFERENCES TO CO-PENDING APPLICATIONS

Continuation of U.S. patent application Ser. No. 07/999,393, filed Dec. 31, 1992, now abandoned, which is a Continuation-In-Part of U.S. patent application Ser. No. 07/704,619, Filed May 23, 1991, titled Implantable Defibrillator System Employing Capacitor Switching Networks (as amended), now U.S. Pat. No. 5,199,429.

FIELD OF THE INVENTION

The present invention is a process for generating waveforms for defibrillating the human heart and the apparatus for generating waveforms, especially the electronic circuitry, including the programming and control accessories.

BACKGROUND OF THE INVENTION

Defibrillating the human heart is accomplished by applying an electrical waveform to the cardiac muscle with appropriate electrodes, causing the cessation of the rapid uncoordinated contractions of the heart, and a restoration of normal beating of the heart.

The optimal voltage-versus-time waveform for this purpose is known approximately, but not precisely. There is wide agreement in the prior art that, at a minimum, it incorporates a rectangular or approximately rectangular positive-going pulse. The adjective "positive-going" has meaning after one has determined the point on or near the heart that best serves as voltage reference for a particular patient, a matter that varies from person to person. In the simplest case, a single such pulse is used for defibrillation. This option is termed the "monophasic" waveform.

For the sake of a concrete description, let one choose a specific waveform that falls in the ranges of accepted values. Such an example is shown in idealized form in FIG. 3. This pulse has an amplitude of +400 volts, and a duration of 7 milliseconds. The literature on this subject is extensive, with a typical example being Feeser, et al., Circulation, volume 82, number 6, page 2128, December, 1990, an article that includes an extensive bibliography.

The electrical resistance presented by the human heart muscle to the passage of defibrillation current is quite low, usually falling in the range from 40 to 100 ohms. These low values are a combined result of the large area electrodes employed and non-linearity to the heart muscle as an electrical resistor, with resistance declining as current increases. Because of this fact, large current values are required, typically several amperes, at the typical but arbitrarily chosen amplitude of 400 V. It is a considerable challenge to generate a rectangular waveform at such a high current, especially in a battery-powered implantable defibrillator system, which must be small and light in weight. Fortunately, an approximation to the idealized waveform is able to accomplish the desired result, but with an effectiveness that is believed to be considerably lower.

A simple and extensively used approximation to the ideal waveform can be achieved by charging a capacitor to 400 volts in the present example, and connecting it directly from one electrode to the other on the heart muscle, and letting the heart serve as the load resistance that discharges the capacitor. When a resistor is used in this manner to discharge a capacitor, the result is a voltage-versus-time waveform that declines in exponential fashion from the initial capacitor voltage, +400 volts at present. The non-linearity mentioned above distorts the exponential waveform somewhat, but not significantly. For purposes of approximating a rectangular waveform, it is necessary to interrupt the discharging process while the voltage remains at some significant fraction of its original value. This can be accomplished by simply breaking, or "opening", the circuit formed by capacitor and resistor, the latter in this case being the heart. At that instant the voltage experienced by the heart drops abruptly to zero.

Assuming for specific illustration that in the 7 ms duration of the pulse, the waveform voltage has dropped to 200 volts, or half its initial value, we see that the "characteristic time" of the discharging process, or the time it takes the voltage to decline to about 36.8% of its initial value, must exceed 7 ms in the present case. The characteristic time in seconds is determined by the product of the resistance R in ohms and the capacitance C in farads. For the assumed requirements, one must achieve a characteristic time, or "RC time constant" of 10 ms. Continuing with specific values for illustrative purposes, let one assume a cardiac resistance of 70 ohms, requiring therefore a capacitance of 143 microfarads. Relationships are illustrated in FIG. 4A for the assumed conditions. The qualitative difference between FIGS. 3 and 4A is known in the jargon of the specialty as the degree of "tilt", and a "low-tilt" waveform is preferred. The approximate waveform is unsatisfactory if the voltage at the end of the pulse interval is a small fraction of the initial voltage, a condition that would be described as a "high-tilt" waveform.

The connection and disconnection of the capacitor to the heart muscle is accomplished in the present state of the art by means of switching networks employing the power field-effect transistor (or FET), by way of example and for purposes of illustration only and not to be construed as limiting of the present invention. This is a three-terminal, solid-state device, with one terminal being a control electrode, and the other two terminals being power electrodes. Resistance between the power terminals can be either very low (the "closed" condition), or very high (the "open" condition). Thus, the FET is functionally equivalent to the familiar mechanical single-pole, single-throw switch, and is described as such for purposes of brevity and illustration. A circuit employing a single such switch can deliver the waveform illustrated in FIG. 4A. Both the waveform and the circuit that produces it, shown in FIG. 4B, are discussed in more detail later.

The first adjective states that this switch incorporates a single pivoted armature or movable lever, and the second adjective means that there is one stable position in which current is conducted. Since description of the switching network is made more easily understood by choosing the mechanical-switch option, as illustrated in FIG. 4B, which schematically presents the network that delivers the result shown in FIG. 4A as later discussed in detail.

Another waveform of the prior art is the "biphasic" waveform, which is capable of achieving defibrillation with less energy than that necessary, with the monophasic waveform. This difference is of prime importance to implantable systems because the total energy deliverable by a battery over its life is approximately proportional to its size and weight.

In a biphasic waveform, a positive pulse of the kind described earlier is followed by a negative pulse. Ideally, the negative pulse should be rectangular, should be comparable in amplitude to the positive pulse, and should have a duration somewhere between 10% and 90% that of the total pulse width. Continuing with specific examples, let one adopt as the positive waveform that of FIG. 5A, where the duration of the negative pulse is shown to be 3 ms. The simplest biphasic switching network of the prior art delivers a negative pulse with an initial amplitude equal to that at the end of the positive pulse, as is illustrated in FIG. 5A. One embodiment of a network for delivering this combined waveform is illustrated in FIG. 5B. This circuit employs two single-pole, triple-throw switches. Such a switch can be realized by using three FETs that all have one power electrode in common. Since the two switches are linked in order to function in coordination, they can be described as a single double-pole, triple-throw switch. Here, c designates the charging position, p the positive-pulse position, and n the negative-pulse position.

The present invention overcomes the disadvantages of the prior art by providing switching networks that provide, for example, discharging of two capacitors in parallel during the positive pulse, and in series during the negative pulse, and that can also be discharged in sequence, if desired.

This change in circuit configuration from two capacitors discharging in parallel to the same two capacitors discharging in series is known as a change in topology. The change from a positive pulse to a negative pulse is known as a change in polarity. The present invention utilizes both changes in topology and changes in polarity to accomplish a unique result.

Straightforward extensions of such principles provide switching networks that employ two or more capacitors, and that provide arbitrary combinations of parallel, series, and sequential discharging of the capacitors, with appropriate control-signal patterns, in order to tailor the resulting waveform into an approximation of any desired ideal waveform, within wide ranges. By similar manipulation of capacitor interconnections, it is possible to capture and use pulse portions that are simply discarded in the prior art, thereby permitting one to achieve certain waveforms with less capacitance than was required before. Because the capacitor is physically the largest component in a prior art defibrillator, reduction in its value and hence size is significant. Such a waveform is illustrated in FIG. 8C. It constitutes a better approximation to the ideal monophasic waveform of FIG. 3 than does the prior art waveform of FIG. 4A, but yet it requires 11% less capacitance than the prior art case. An alternative method of more closely approximating the ideal waveform of FIG. 3 is to change topology and polarity of the circuit at different times to take advantage of the various waveforms that can be generated by such independent switching.

To accomplish control and setting of the switching network from outside the body, it is foreseen that digital programming through, for example, RF electromagnetic radiation, will be used as it now is for other systems such as pacemakers. It is further provided that a telemetry relay positioned at or on the body can be employed to facilitate the digital programming. It is further proposed that photovoltaic devices be subcutaneously implanted to charge the implanted batteries. Particularly useful here are series-array "solar" cells, with the monolithic series-array versions of the prior art being especially well adapted. A further option, of course, is the use of an implanted coil as in the prior art that is powered by an external source of electromagnetic radiation.

SUMMARY OF THE INVENTION

The general purpose of the invention is to realize an implantable defibrillator system that provides waveform optimization before or after implantation, that has a long useful implanted life, and that is smaller in size than previous implantable defibrillators. Part of the novelty resides in the design of switching networks for waveform tailoring.

One embodiment of the present invention provides two or more capacitors that can, by a switching network, be discharged in parallel, doubling the current and reducing the tilt, or else can be discharged in series, or in sequence. When the capacitors are discharged in series to provide the negative pulse, it is possible to boost negative-pulse amplitude to approximate that of the positive pulse. Or, the capacitors can be discharged in parallel for less tilt when a diminished amplitude is acceptable. Additionally, the topology and polarity of the circuit can be changed independent of one another. Changing the topology from parallel capacitor discharge to series capacitor discharge just prior to the polarity change produces a sharp positive spike just prior to the negative pulse, thereby more nearly squaring the overall positive pulse to the heart.

In extensions of the present invention, more than two capacitors may be used, and series, parallel, and sequential capacitor-discharge configurations can be optionally combined to tailor a waveform conforming as nearly as possible to the ideal waveform that will be perceived as the defibrillation art progresses. A novel feature of replacing one large capacitor by two or more smaller capacitors of the same aggregate capacitance bring design flexibility advantages. For example, the smaller components can be packed more densely, leading to smaller overall package size. This is because the large capacitors used in this work have an inflexible cylindrical form factor. Another novel feature is a reduction in the amount of capacitance needed to generate certain waveforms, and hence a further size reduction.

Added to the novelty of the implanted defibrillator system is the combination of the above features with digital programming through rf communication of the kind used in pacemakers. Further combinational novelty includes a telemetry relay to permit the programming electronics and its operator to be spatially removed from the operating theater where implantation of the defibrillator system is performed.

A still further novelty resides in the use of implantable batteries, because of the appreciable energy demands over time of defibrillator systems. Because of the relatively high voltage requirements of a defibrillator system, the invention further employs implanted series-array (and hence high-voltage) photovoltaic devices, with monolithic series-array varieties being particularly favored for reasons of reliability and efficiency. Recharging by this means brings with it the novel and attractive features of being non-invasive, inexpensive, and simple to the point of being simplistic with respect to the demands that recharging places on the patient or the medical attendant.

One significant aspect and feature of the present invention is the discharging of defibrillation capacitors in parallel, in series, or in sequence, as desired, through novel switching networks.

Another significant aspect and feature of the present invention increases the number of capacitors further, and through novel switching networks, provides arbitrary combinations of parallel, series, and sequential discharging of arbitrary combinations of the capacitors, thereby tailoring the defibrillation waveform with a high degree of flexibility. A control system controls the switching network to achieve the desired waveform.

An additional significant aspect and feature of the present invention is the realization of certain waveforms with less total capacitance than required in the prior art, thereby making possible a smaller implantable defibrillator because the capacitor is such a dominant component in an implantable defibrillator. Thus, the use of smaller but multiple capacitors contributes in two ways to the size reduction of an implantable defibrillator.

Still another significant aspect and feature of the present invention is the digital programming of the control system from outside the body, with an RF transmission being one possible form of communication for the purpose. A telemetry system can be placed at or near the body of the person having the implant.

Having thus described the embodiments of the present invention, it is one object of the present invention to achieve defibrillator-waveform flexibility, to adapt to changes in the patient's needs, or to adapt to advancing knowledge of the defibrillation art.

Another object of the present invention is to achieve a system of long life and high reliability for the implantable defibrillator system.

An additional object of the present invention is to realize a smaller implantable defibrillator package than that of a prior art defibrillator of equal capability.

Yet another object of the present invention is to ensure that the patient's portion of the routine maintenance technology is simple, easy-to-use, nonhazardous, and low-technology in character, especially as to battery recharging.

BRIEF DESCRIPTION OF THE DRAWINGS

FIG. 6A illustrates a monophasic waveform of the present invention resulting from the sequential discharging of two capacitors;

FIG. 6B schematically illustrates a circuit for generating the sequential-discharge monophasic waveform of the present invention;

FIG. 6C illustrates a monophasic waveform of the present invention resulting from the sequential discharging of four capacitors;

DETAILED DESCRIPTION OF THE INVENTION

Figure 1:
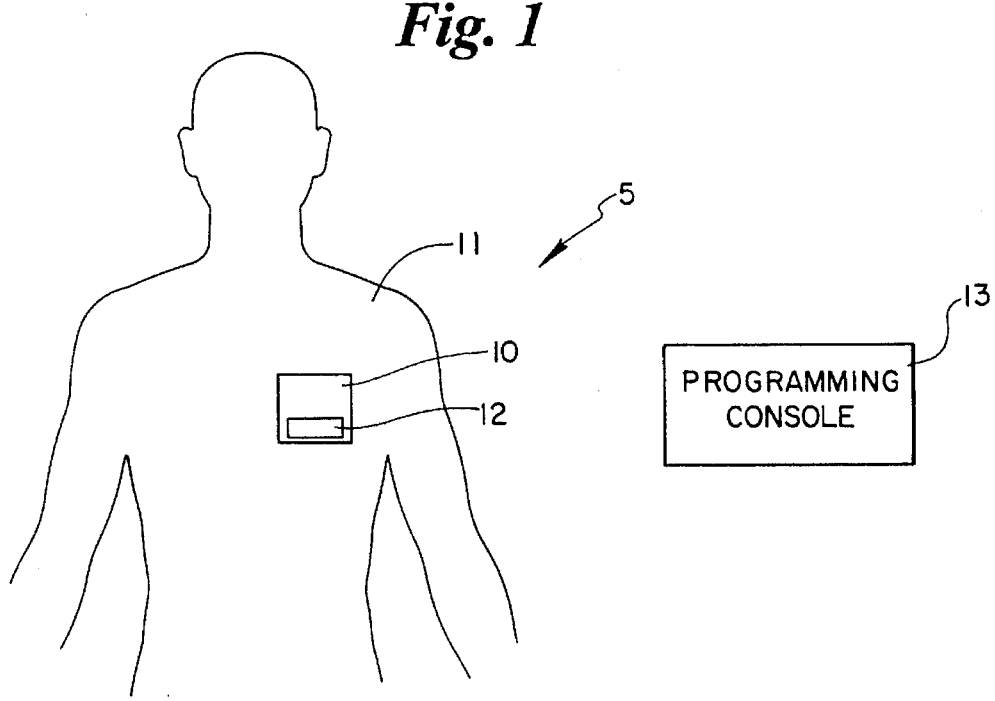
FIG. 1 illustrates an implantable defibrillator system implanted in a patient and an external programming console.

FIG. 1 illustrates an implantable defibrillator system 5, such as an implantable defibrillator 10 in a patient 11, the implantable defibrillator 10 in turn including an electronic switching network 12 for the flexible combination of capacitor discharge waveforms in order to approximate a particular waveform for application to the heart muscle in a defibrillation procedure. A programming console 13 that is able to compute and transmit instructions to the electronic switching network 12 is comparatively remote from the patient 11 who is undergoing implantation surgery, and a telemetry relay or repeater is employed near or on the patient's body. Digital signals are transmitted to the implanted device using infrared, visible or RF electromagnetic radiation or ultrasound radiation.

Figure 2:
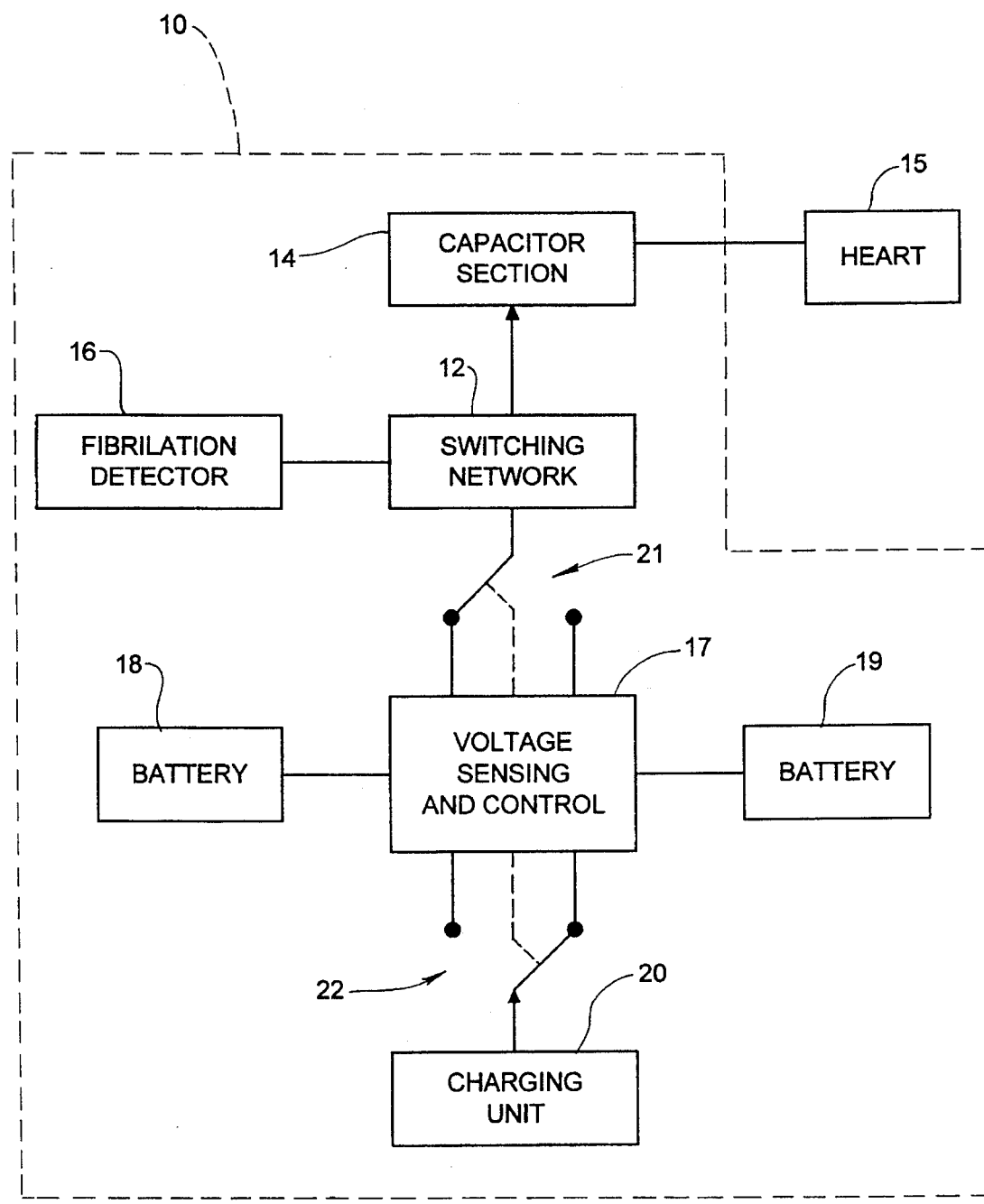
FIG. 2 illustrates a block diagram of the implantable defibrillator system.

FIG. 2 illustrates the implantable defibrillator 10 where all numerals correspond to those elements previously described, including a capacitor section 14 electrically connected through electrodes to a heart 15, an electronic switching network 12, a committed or non-committed fibrillation detector 16, a voltage sensing and entirely unit 17, batteries 18 and 19 connected through the voltage sensing and control unit 17 to the electronic switching network 12, and a charging unit 20. As illustrated, battery 18 is connected through the voltage sensing and control unit 17 to the electronic switching network 12 and its associated components. The battery 19 is being recharged through the voltage sensing and control unit 17 by the charging unit 20. When battery 18 is deeply discharged, the voltage sensing and control unit 17 switches the output of the charging unit 20 to battery 18 and switches the output of the battery 19 to the electronic switching network 12, as represented by the reversal of representative switches 21 and 22. At this time, battery 18 is urged and battery 19 powers the implantable defibrillator 10. The charging unit 20, when it employs photovoltaic devices, can be a subcutaneously implanted device that is powered from an external light source, and can be implanted subcutaneously or more deeply when it is a evil to which energy is delivered from an external source of electromagnetic radiation.

Figure 3:
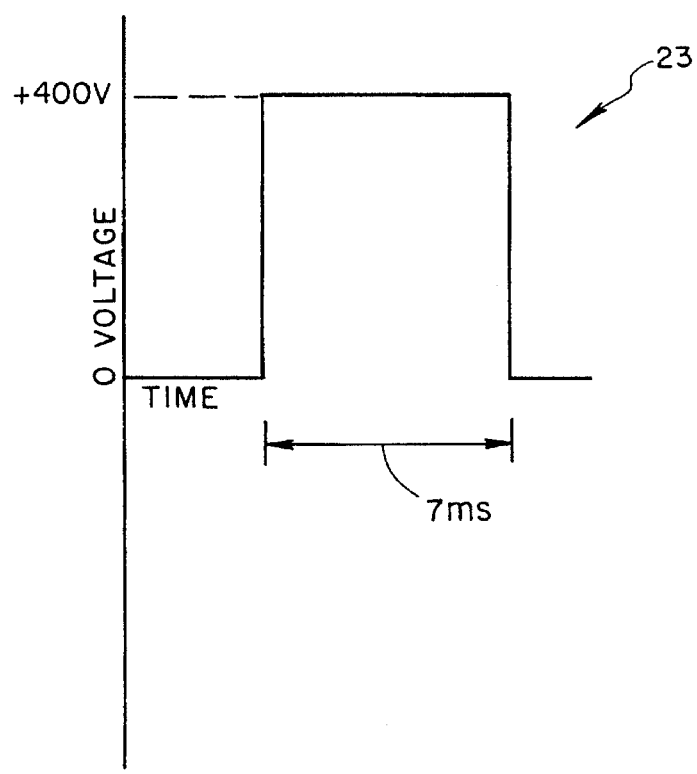
FIG. 3 presents the idealized waveform for monophasic defibrillation.

FIG. 3 illustrates a voltage-versus-time waveform 23 that is of idealized rectangular character, having typical, but arbitrarily chosen, amplitude of +400 volts and duration of 7 milliseconds. The waveform consists of a single pulse and it is termed monophasic.

Figure 4A:
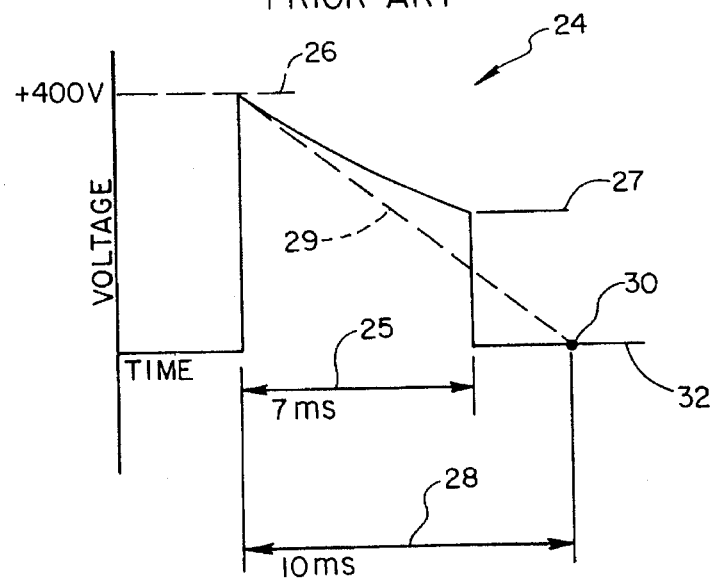
FIG. 4A shows a prior art monophasic waveform, achieved through capacitor discharge and switching.

FIG. 4A illustrates prior art voltage-versus-time monophasic waveform 24, the type generated by a charged capacitor, appropriately switched. Realistic and arbitrary pulse duration 25 are again employed. The initial pulse voltage 26 is fixed by the voltage to which the capacitor is charged, and the final pulse voltage 27 is fixed by the discharge rate, the RC time constant 28, which can be graphically determined by linear extrapolation of the initial tangent 29 to the point 30 where the tangent intersects the time axis 32.

Figure 4B:
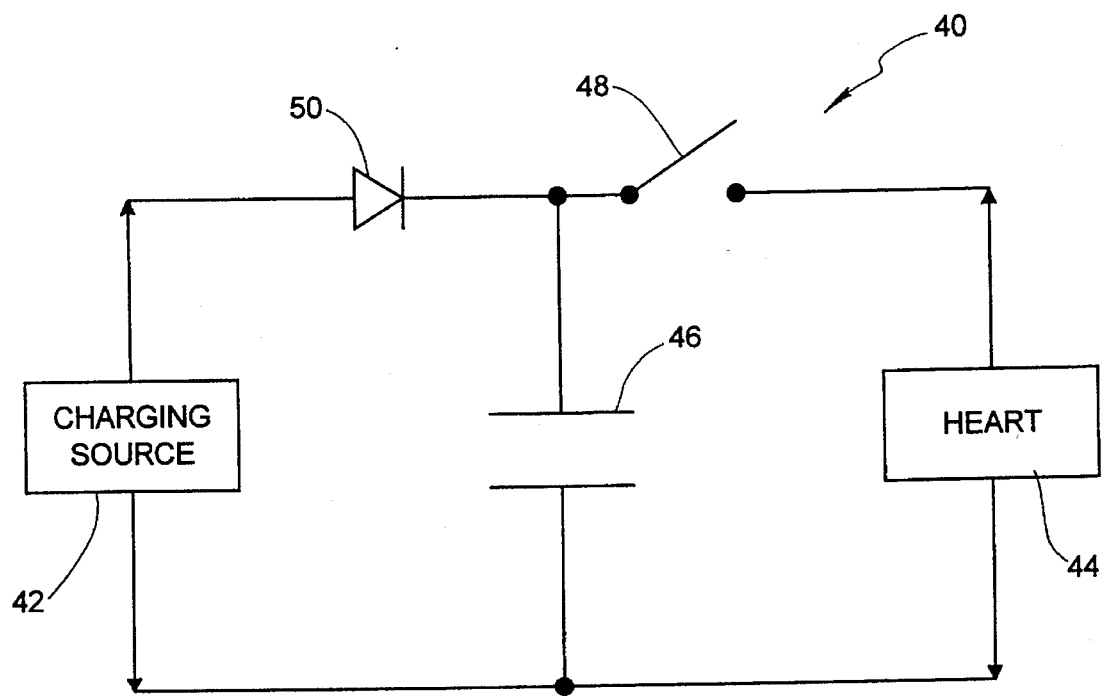
FIG. 4B schematically illustrates a circuit for achieving the prior art monophasic waveform.

FIG. 4B illustrates a prior art schematic diagram 40 of a circuit placed between a charging source 42 and a heart 44, for generating the prior art monophasic waveform 24 of FIG. 4A, employing a capacitor 46, a single-pole, single-throw switch 48, and a diode 50.

Figure 5A:
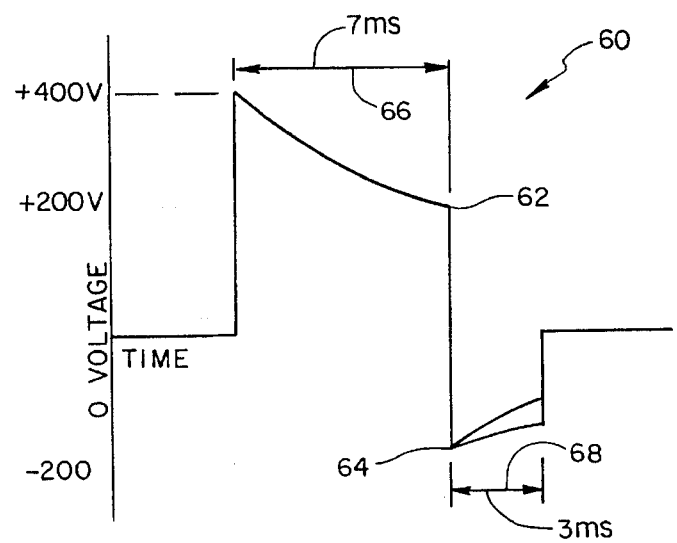
FIG. 5A presents a prior art biphasic waveform.

FIG. 5A illustrates a biphasic waveform 60 of the prior art, wherein the final height 62 of the positive pulse, +200 volts, is equal in magnitude and opposite in sign to the initial height 64 of the negative pulse, −200 volts. Typically, and arbitrarily, by way of example and for purposes of illustration only and not to be construed as limiting of the present invention, chosen durations for the two pulses are 7 ms 66, and 3 ms 68, respectively.

Figure 5B:
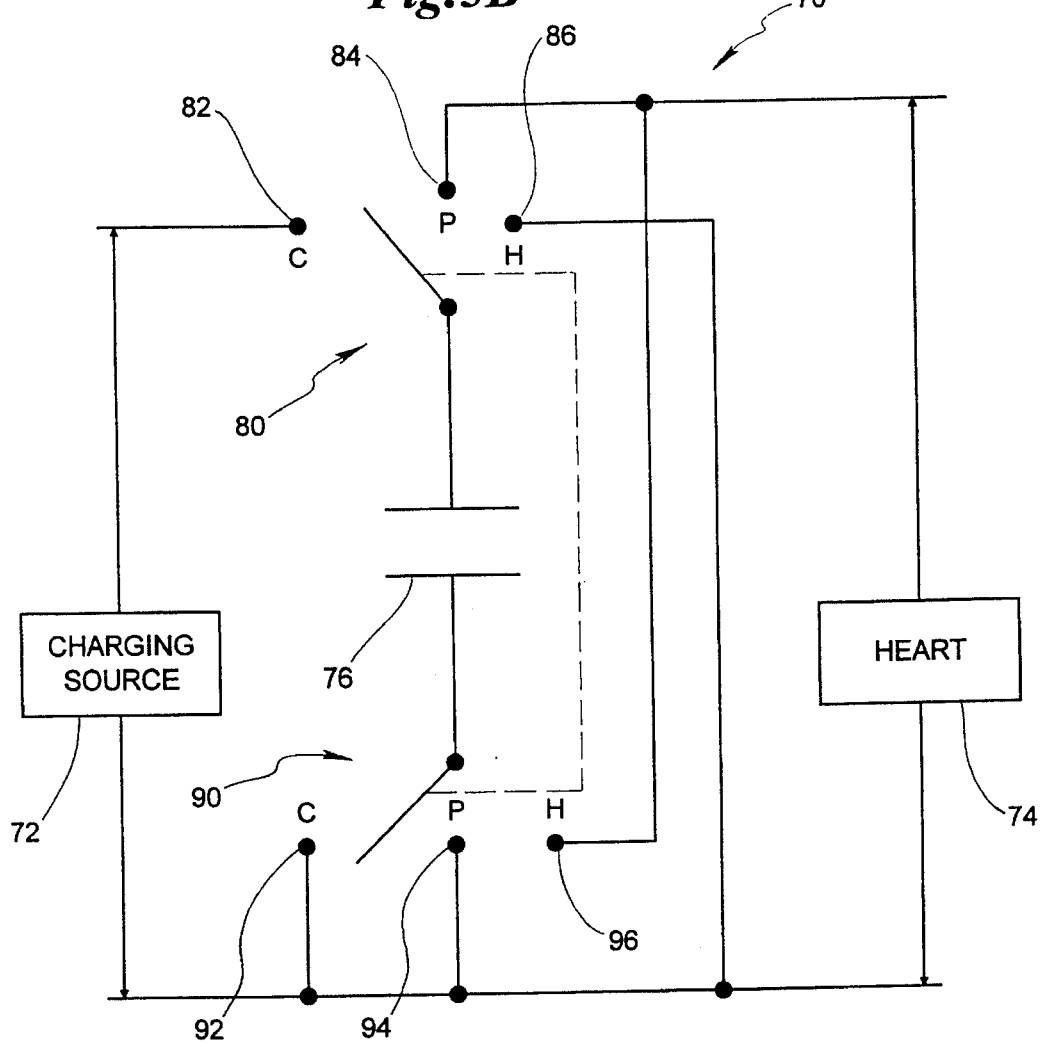
FIG. 5B schematically illustrates a circuit for generating a prior art biphasic waveform.

FIG. 5B illustrates the schematic diagram 70 of a circuit placed between a charging source 72 and a heart 74, for generating the biphasic waveform 60 of FIG. 5A, employing a capacitor 76 and the single-pole, triple throw switches 80 and 90. Switches 80, 90 may, in combination be alternatively described as one double-pole, triple-throw switch. The three positions of the switch 80 are c, the charging position 82, b, the positive-pulse position 84, and n, the negative-pulse position 86. The corresponding positions of the switch 90 are c, the charging position 92, b, the positive pulse position 94, and n, the negative-pulse position 96.

FIG. 6A illustrates a monophasic waveform 100 of the present invention generated by the sequential discharging of two capacitors having an aggregate capacitance equal to that of capacitor 46 in FIG. 4B, and featuring two maxima or peaks 102 and 104, thus providing a monophasic waveform 100 that is a better approximation to the ideal waveform 23 of FIG. 3 than is the prior art waveform 24 of FIG. 4A.

FIG. 6B illustrates the schematic diagram 105 of a circuit placed between a charging source 106 and a heart 107, for generating the waveform 100 of FIG. 6A, employing capacitors 108 and 109 and the single-pole, triple-throw switches 110 and 120 (which switches in combination can alternatively be described as one double-pole, triple-throw switch). The three positions of the switch 110 are c, the charging position 112, pa, the position 114 for the first half of the positive pulse, and pb, the position 116 for the second half of the positive pulse. The corresponding positions of the switch 120 are c, the charging position 122, pa, the position 124 for the first half of the positive pulse, and pb, the position 126 for the second half of the positive pulse.

FIG. 6C illustrates a monophasic waveform 130 of the present invention generated by the sequential discharging of four capacitors having an aggregate capacitance equal to that of capacitor 46 in FIG. 4B, and featuring four maxima or peaks 132, 134, 136, and 138, using a circuit that is a straight forward extension of that in FIG. 6B, and providing a waveform 130 that is a better approximation of the ideal waveform 23 of FIG. 3 than is the prior art waveform 24 of FIG. 4A.

Figure 7A:
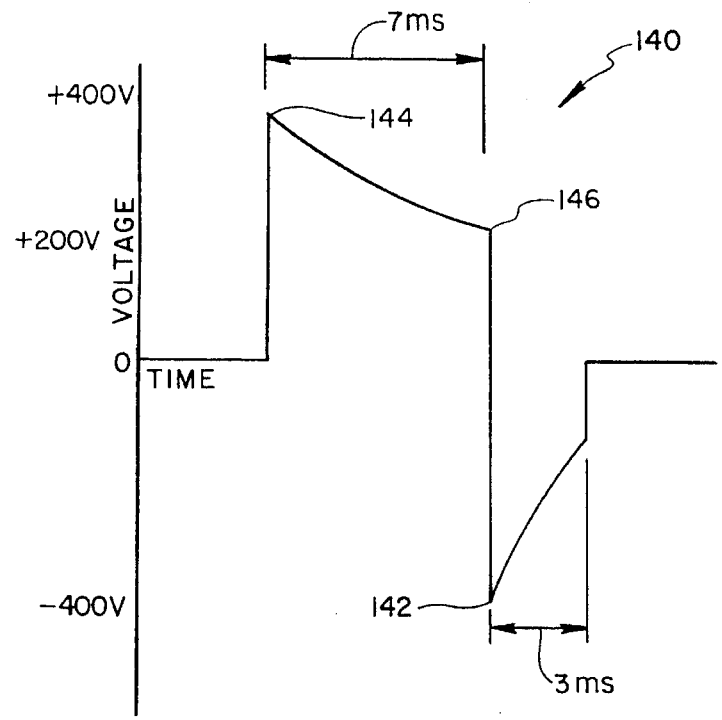
FIG. 7A illustrates one biphasic waveform of the present invention.

FIG. 7A illustrates a biphasic waveform 140 of the present invention, wherein the initial height 142 of the negative pulse is comparable in magnitude to the initial height 144 of the positive pulse, and is greater in magnitude than the final height 146 of the positive pulse thus providing more nearly ideal waveform than the prior art waveform 60 of FIG. 5A.

Figure 7B:
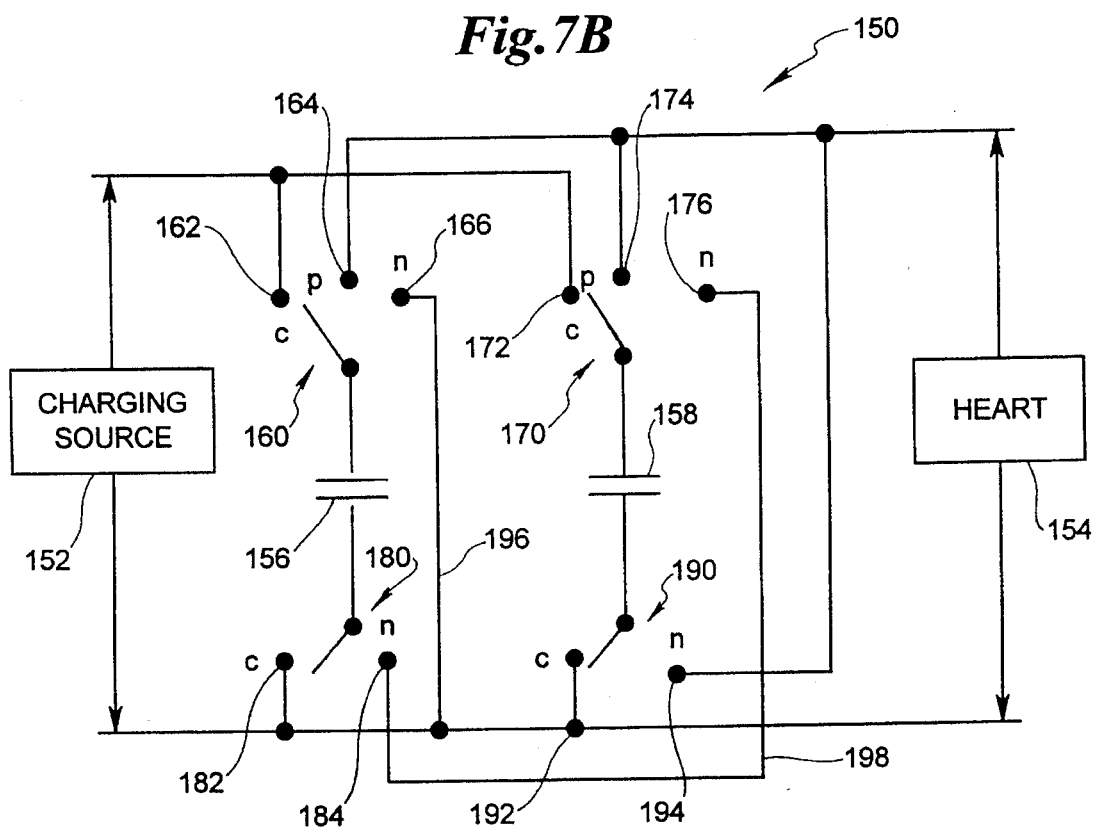
FIG. 7B schematically illustrates a circuit for producing one biphasic waveform of the present invention.

FIG. 7B illustrates the schematic diagram 150 of the circuit placed between a charging source 152 and a heart 154 for generating the waveform 140 of FIG. 7A, employing the capacitors 156 and 158, two single-pole, triple-throw switches 160 and 170 (which switches in combination can alternatively be described as one double-pole, triple-throw switch), and also two single-pole, double-throw switches 180 and 190 (which switches in combination can alternatively be described as one double-pole, double-throw switch). The three positions of the switch 160 are c, the charging position 162, p, the positive-pulse position 164, and n, the negative pulse position 166. The corresponding positions of the switch 170 are the c, charging position 172, p, the positive-pulse position 174, and n, the negative-pulse position 176. The two positions of the switch 180 are c, the charging and positive pulse position 182, and n, the negative pulse position 184. The corresponding positions of the switch 190 are c, the charging and positive pulse position 192, and n, the negative-pulse position 194. The interconnecting leads 196 and 198 achieve the capacitor "stacking" (series connection) and polarity reversal required for the negative pulse.

Figure 8A:
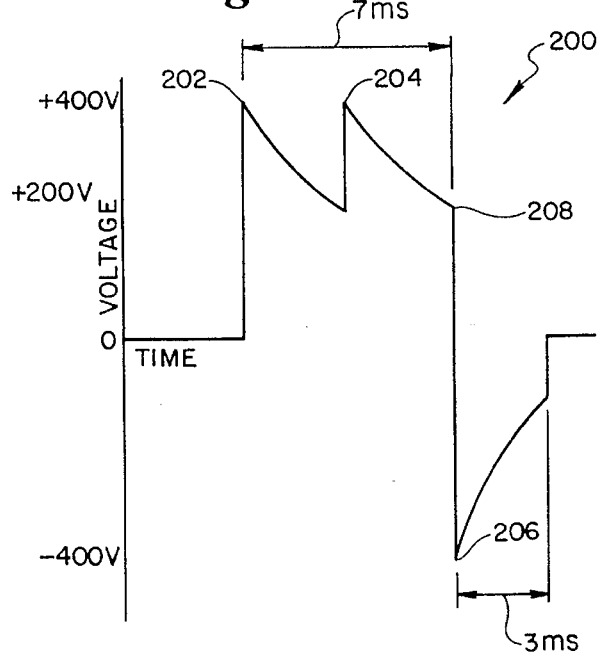
FIG. 8A illustrates another biphasic waveform of the present invention, incorporating sequential discharging.

FIG. 8A illustrates a biphasic waveform 200 of the present invention, wherein there are two peaks 202 and 204 in the positive pulse, and wherein the initial height 206 of the negative pulse is comparable in magnitude to that of the initial height 207 of the positive pulse, and is greater in magnitude than the final height 208 of the positive pulse, thus providing a more nearly ideal waveform than the prior art waveform 60 of FIG. 5A.

Figure 8C:
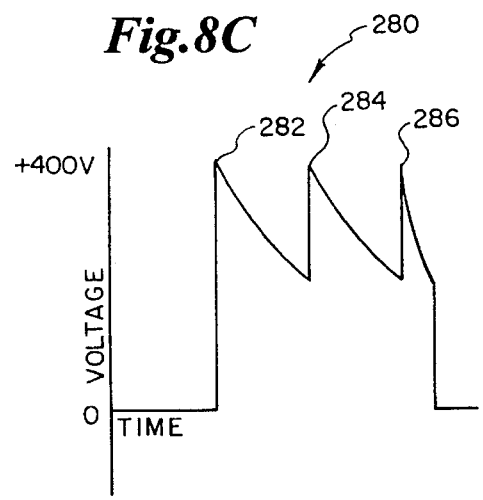
FIG. 8C illustrates yet another monophasic waveform of the present invention.
Figure 8B:
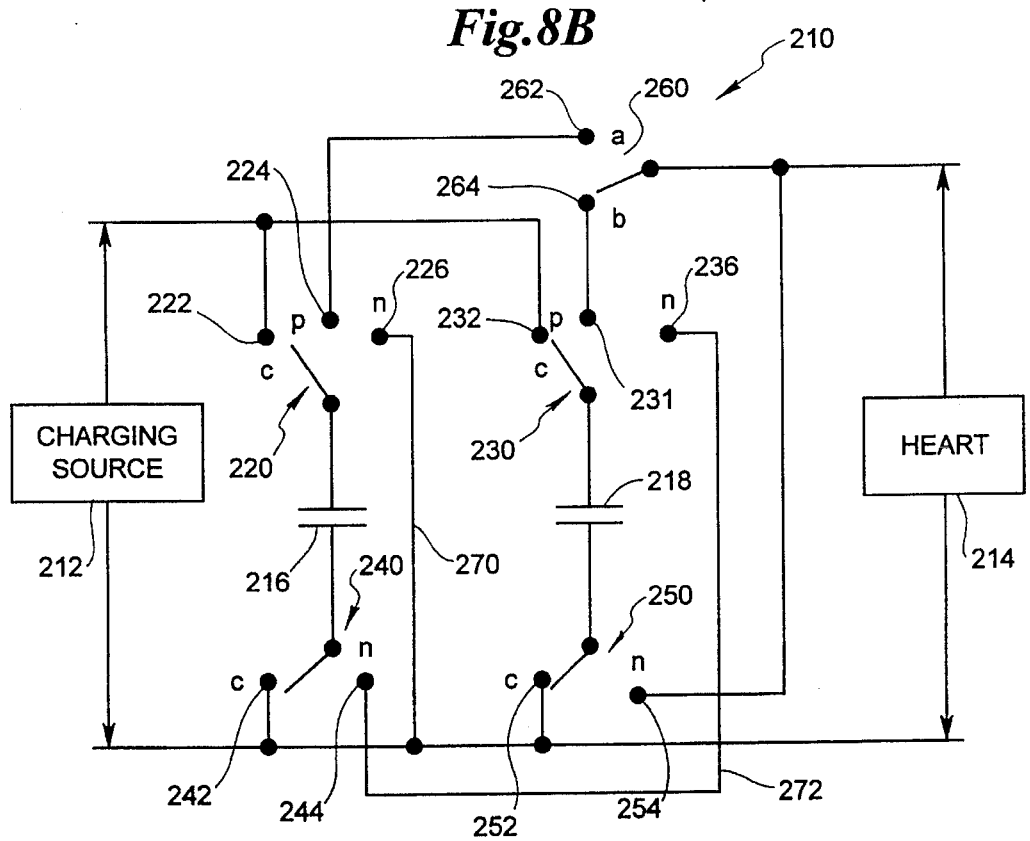
FIG. 8B schematically illustrates a circuit for generating another biphasic waveform of the present invention.

FIG. 8B illustrates the schematic diagram 210 of a circuit placed between a charging source 212 and a heart 214, for generating the waveform 200 of FIG. 8A, employing the capacitors 216 and 218, and the single-pole, triple-throw switches 220 and 230 (which switches in combination can alternatively be described as one double-pole, triple-throw switch), and also the single-pole, double-throw switches 240 and 250 (which switches in combination can alternatively be described as one double-pole, double-throw switch), as well as the single-pole, double-throw switch 260. The three positions of the switch 220 are c, the charging position 222, p, the positive-pulse position 224, and n, the negative-pulse position 226. The corresponding positions of the switch 230 are c, the charging position 232, p, the positive-pulse position 234, and n, the negative-pulse position 236. The two positions of the switch 240 are c, the charging and positive pulse position 242, and n, the negative-pulse position 244. The corresponding positions of the switch 250 are c, the charging and positive pulse position 252 and n, the negative-pulse position 254. The two positions of the switch 260 are a, the position 262 for the first half of the positive pulse during which the capacitor 216 is discharged, and b, the position 264 for the second half of the positive pulse, during which the capacitor 218 is discharged. The interconnecting leads 270 and 272 achieve the capacitor "stacking" and polarity reversal required for the negative pulse.

FIG. 8C illustrates a monophasic waveform 280 of the present invention, wherein the first peak 282 is generated by discharging a first capacitor, the second peak 284 is generated by discharging a second capacitor, and the third peak 286 is generated by placing the two capacitors in series and continuing the discharge by using a circuit that is like circuit 210 of FIG. 8B, but with the polarity-reversing feature eliminated, with the result that the waveform 280 is a better approximation of the ideal waveform 23 of FIG. 3 than is the prior art waveform 24 of FIG. 4A, and yet the sum of the capacitances of the two capacitors is smaller than that of the capacitor 46 in FIG. 4B.

Figure 9:
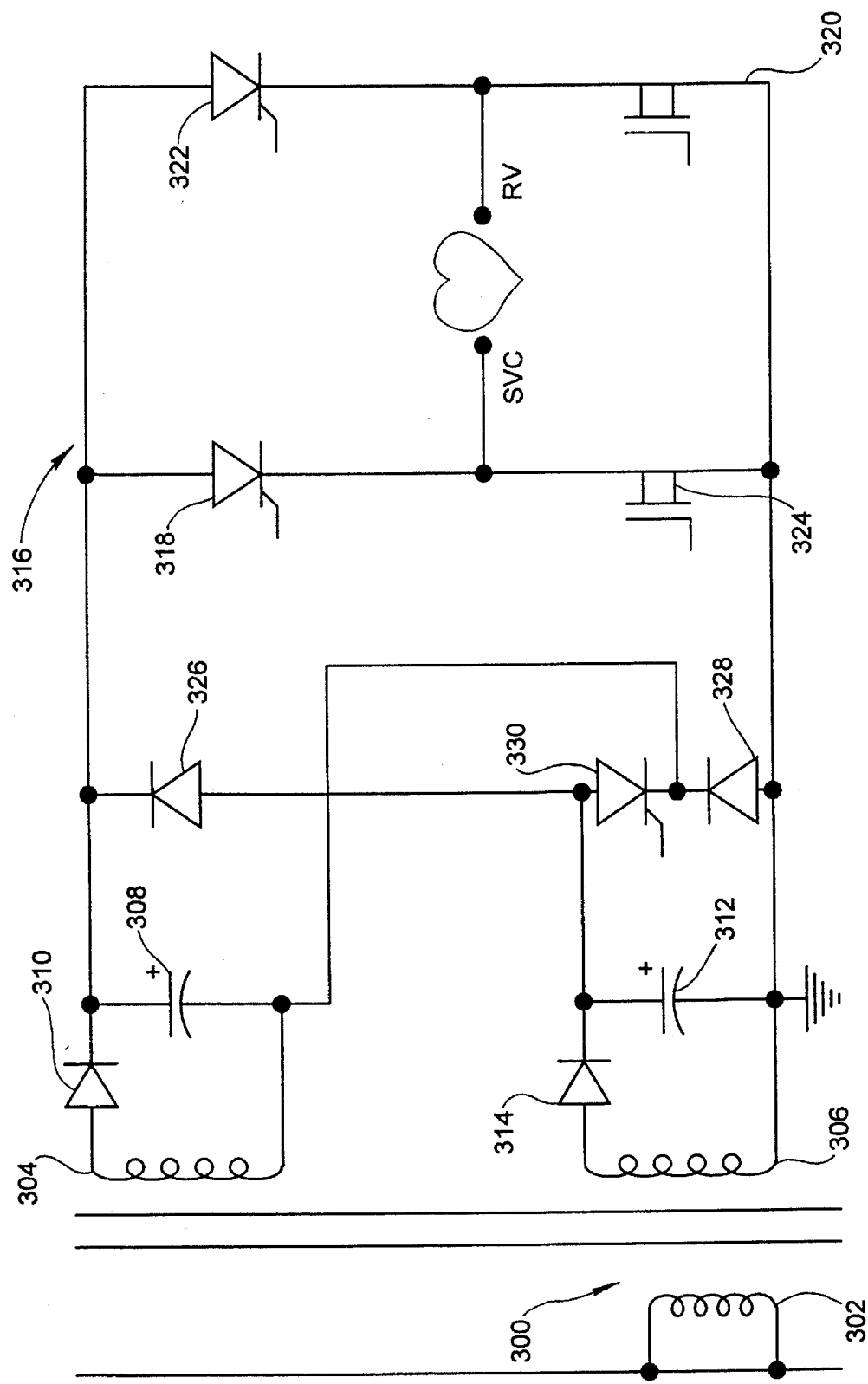
FIG. 9 illustrates a circuit diagram of a circuit capable of producing a biphasic waveform of the present invention.

FIG. 9 illustrates a circuit that is capable of producing waveforms of the present invention and achieves the circuit represented schematically in FIGS. 6B, 7B, and 8B. Transformer 300 provides the power source to charge the circuit.

Transformer 300 has a primary winding 302 and two secondary windings 304, 306. Secondary winding 304 charges capacitor 308 through diode 310. Secondary winding 306 charges capacitor 312 through Diode 314. The H bridge circuit 316 is of conventional design.

For the positive pulse phase, semiconductor switches 318 and 320 are turned on. To change polarity to the negative pulse phase, switches 322 and 324 are turned on.

For parallel discharging of capacitors 308 and 312, capacitor 308 is discharged through diode 326 and capacitor 312 is simultaneously discharged directly through H bridge 316 and back through diode 328.

To change the topology from parallel capacitor discharge to series capacitor discharge, SCR switch 330 is turned on. This serves to discharge capacitor 312 through the negative terminal of capacitor 308, thus placing capacitors 308 and 312 in a series configuration.

The topology and polarity changes just described may be done simultaneously or independently. It may be optimal, for a given patient, to make the topology change prior to the polarity change or make the polarity change prior to the topology change.

Figure 10:
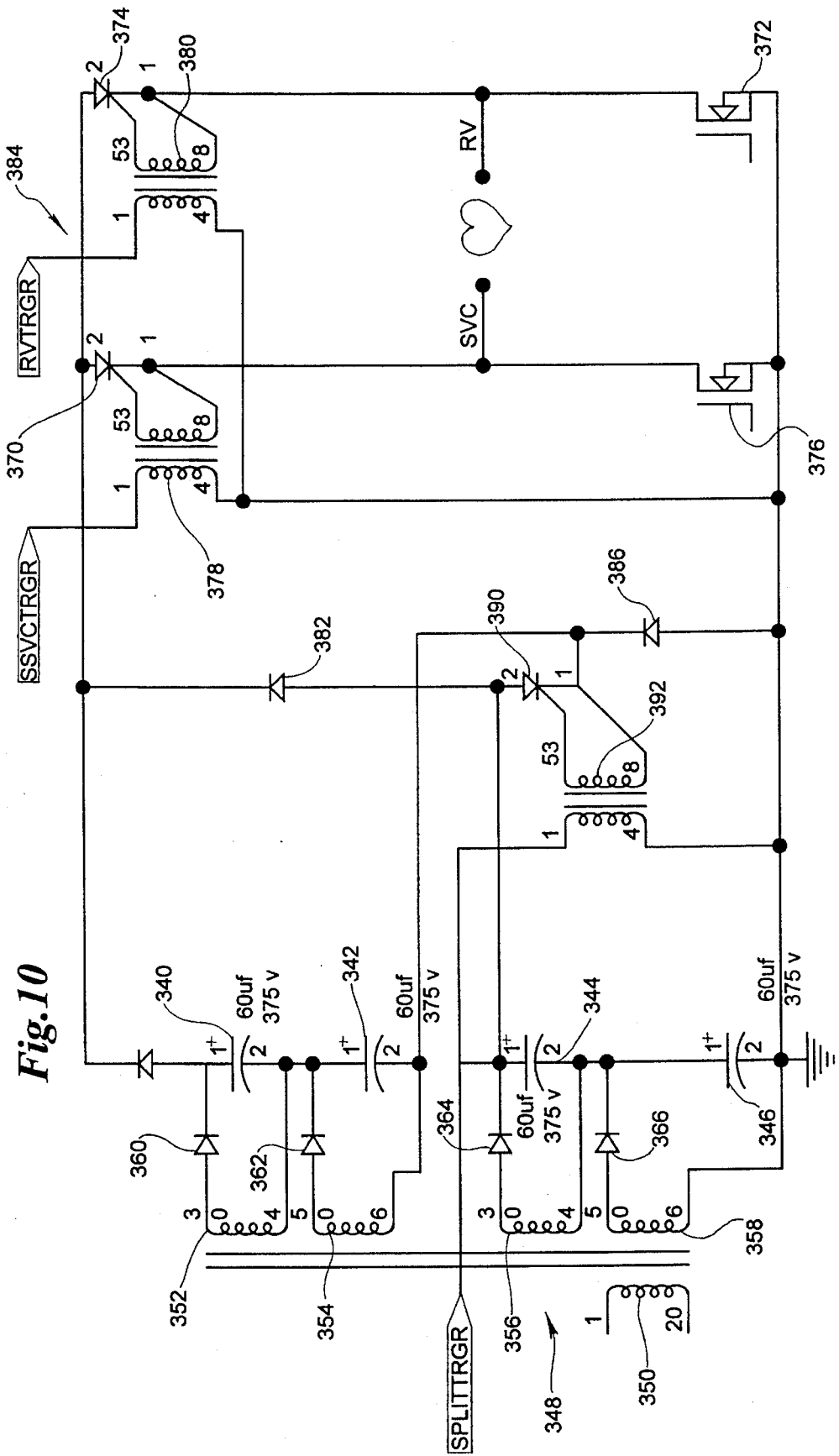
FIG. 10 illustrates another circuit diagram of a circuit capable of producing a biphasic waveform of the present invention.

FIG. 10 illustrates a novel alternative circuit to provide waveforms of the present invention. This circuit is substantially identical in its waveform product to the circuit depicted in FIG. 9. At present, efficient capacitors capable of high enough voltage operation to be sufficient for defibrillation are not available with the sufficient compactness necessary for implantation in a human. Accordingly, to realize the necessary high voltage, two capacitors are utilized in series to provide the output that is desired from a single efficient capacitor, where such efficient capacitor is presently available. Accordingly, the circuit of FIG. 10 includes capacitors 340, 342, 344, and 346. Each capacitor 340, 342, 344, and 346 is preferably a 60 μF, 375 v capacitor. Capacitors 340 and 342 are connected in series and function together as a single capacitor of 750 v. Capacitors 344 and 346 are also connected in series and function together as a second single capacitor of 750 v. The series connections just described are not affected during the topology change that is made to effect the desired waveforms of the present invention. The topology changes affect the relationship of the capacitor unit comprised of capacitors 340 and 342 with respect to the capacitor unit comprised of capacitors 344 and 346.

Transformer 348 has a primary winding 350 and four secondary windings 352, 354, 356, and 358. Secondary winding 352 charges capacitor 340 through diode 360. Secondary winding 354 charges capacitor 342 through diode 362. Secondary winding 356 charges capacitor 344 through diode 364. And, secondary winding 358 charges capacitor 346 through diode 366.

For the positive pulse phase, semiconductor switches 370 and 372 are turned on. To change polarity to the negative pulse phase, switches 374 and 376 are turned on. The switching of semiconductor switch 370 is controlled by transformer 378 and the switching of semiconductor switch 374 is controlled by transformer 380.

For parallel discharging of the capacitor unit made up of capacitors 340, 342 and the capacitor unit made up of capacitors 344, 346, the capacitor unit made up of capacitors 340, 342 is discharged through diode 382 and the capacitor unit made up of capacitors 344, 346 is simultaneously discharged directly through H bridge 384 and back through diode 386.

To change the topology from parallel capacitor discharge to series capacitor discharge, semiconductor switch 390 is turned on by transformer 392. This serves to discharge the capacitor unit made up of capacitors 344, 346 through the negative terminal of the capacitor unit made up of capacitors 340, 342, thus placing the capacitor unit made up of capacitors 340, 342 and the capacitor unit made up of capacitors 344, 346 in a series configuration. Thus, the parallel topology is actually a two by two arrangement, where two capacitors in series are in parallel with two capacitors in series. The series topology then is four capacitors in series.

The topology and polarity changes just described may be done simultaneously or independently. It may be optimal, for a given patient, to make the topology change prior to the polarity change or make the polarity change prior to the topology change.

Figure 11A:
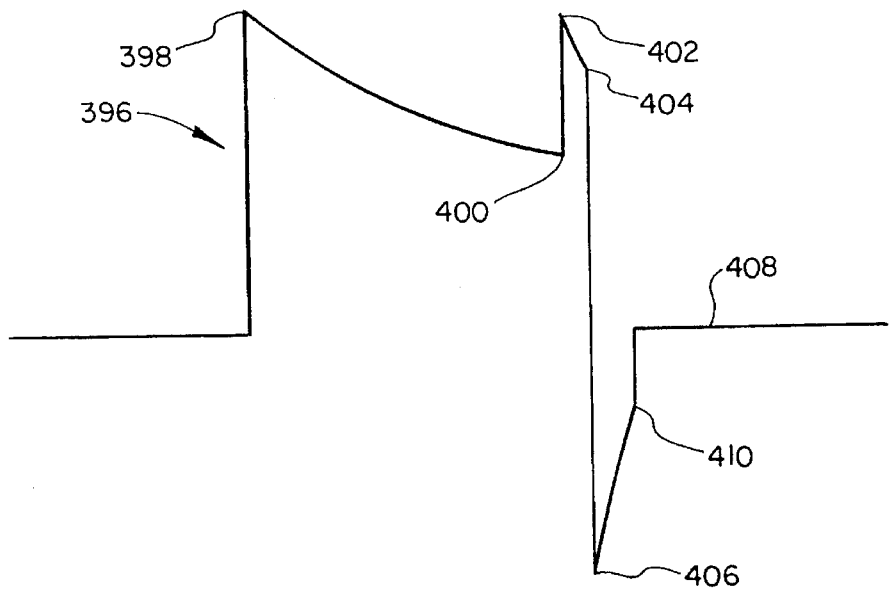
FIG. 11A illustrates a biphasic waveform in which the topology is switched prior to the polarity being switched.

FIG. 11A illustrates a biphasic waveform 396 of the present invention in which the topology conversion is made prior to the polarity conversion. Peak 398 is produced by the discharge of two capacitors or capacitor units in parallel. A circuit such as depicted in FIG. 10 produces a peak 398 of 750 volts. The discharge of two capacitors or capacitor units in parallel decay relatively slowly to the point 400. At point 400, the voltage is suddenly doubled to peak 402 when the two capacitors or capacitor units are put in series. The decay of the voltage is much more rapid in the series topology and drops relatively quickly to point 404. At point 404, the polarity of the circuit is changed from positive to negative and the voltage suddenly changes to the same magnitude in the negative direction at peak 406. The voltage continues to decay rapidly toward the zero voltage line 408 and is terminated at point 410 and the voltage to the heart drops to zero.

Figure 11B:
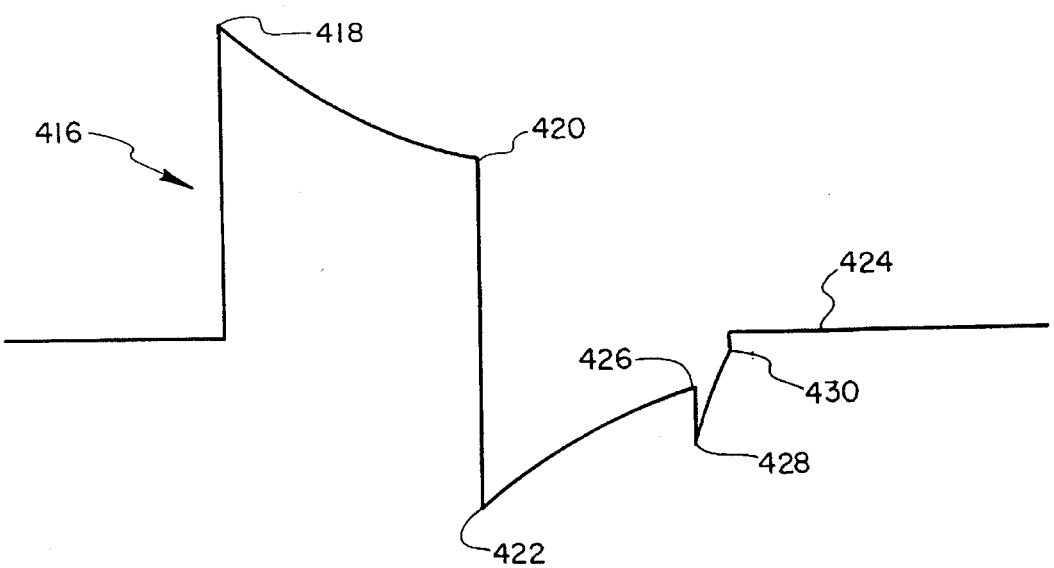
FIG. 11B illustrates a biphasic waveform in which the polarity is switched prior to the topology being switched.

FIG. 11B illustrates a biphasic waveform 416 of the present invention in which the polarity conversion is made prior to the topology conversion. Peak 418 is produced by the discharge of two capacitors or capacitor units in parallel. A circuit such as depicted in FIG. 10 produces a peak 418 of 750 volts. The discharge of two capacitors or capacitor units in parallel decay relatively slowly to the point 420. At point 420, the voltage is suddenly changed to the same magnitude in the negative direction at peak 422 when the polarity of the circuit is changed from positive to negative. The voltage continues to decay slowly toward the zero voltage line 424. At point 426, the voltage is suddenly doubled to peak 428 when the two capacitors or capacitor units are put in series. The decay of the voltage is much more rapid in the series topology and drops relatively quickly to point 430, where the voltage is terminated and drops to zero.

Mode of Operation

Waveform tailoring is accomplished by instantaneous switching that converts parallel connected capacitors into series-connected capacitors, or the reverse, and/or interchanges of the capacitor terminal connections. Such manipulation of capacitor interconnection also makes possible a reduction in the total capacitance required to achieve certain waveforms, and hence a reduction in defibrillator size. Power FETs can be used for switching, and are controlled by digital signals. The necessary high or low control voltage is distributed from the switching network that can be digitally programmed. The electronics needed for programming of the implantable defibrillator system need not be implanted, but can be a part of the programming console. Input information to the programming console takes the form of the desired initial voltage of the positive pulse, pulse duration and the tilt, and likewise corresponding data for the negative pulse.

In the programming console is the necessary logic and memory, or if needed, ancillary microcomputer hardware and software, that converts the waveform information into digital instructions. The programming console can be comparatively remote from the patient who is undergoing implantation surgery when telemetry relay or a telemetry repeater is employed near or on the patient's body. Foreseen is the use of infrared or radio-frequency electromagnetic radiation, or ultrasound radiation for remote programming purposes. The radiation can be directed along a single line of sight, or can be diverted by means of passive reflector repeater mirrors.

The Switching Networks

Novel switching networks are a part of the present invention of the implantable defibrillator system. The principles can be illustrated by observing the waveform features illustrated in FIG. 7A. Here, each of the two capacitors of FIG. 7B are used in a novel manner. During the positive pulse, the two capacitors are discharged in parallel, producing a positive pulse result equivalent to that in FIG. 4A and FIG. 6A. The negative pulse is generated by placing the two capacitors in series, providing an initial negative pulse height equal in magnitude to the initial positive pulse height. Because two identical capacitors in series display one quarter of the capacitance of the same two capacitors in parallel, the discharge rate of the negative pulse in FIG. 7A is four times that of the positive pulse in FIG. 7A. The increased tilt is believed to be tolerable because the negative pulse is of relatively short duration. The schematic diagram in FIG. 7B illustrates a circuit that delivers the waveform of FIG. 7A, with the designations c for charging, p for positive-pulse position, and n for negative-pulse position having the same meanings as before.

Another two-capacitor embodiment of the present invention produces a two-peaked waveform illustrated in FIG. 6A by discharging two capacitors in sequence, yielding a waveform that is functionally nearer the ideal waveform of FIG. 3 than is the prior art monophasic waveform of FIG. 4A. This is accomplished by the circuit shown schematically in FIG. 6B. Straightforward extension of the principle adds capacitors and switches to this circuit to produce multiple peaks, as in the four-peak example shown in FIG. 6C. This option leads to a smaller implantable defibrillator, because the smaller capacitors can be packed more densely than with the single larger capacitor, which has an inflexible cylindrical form factor, and is the largest component in the circuit, larger even than the battery.

A specific embodiment of another two-capacitor configuration of the present invention yields the waveform illustration in FIG. 8A. Here, the two capacitors illustrated in FIG. 8B are discharged in sequence during the positive pulse, as in FIGS. 6A and 6B, and are discharged in series during the negative pulse, as in FIGS. 7A and 7B. The circuit of the present invention illustrated schematically in FIG. 8B delivers the waveform of FIG. 8A. By eliminating the polarity-reversing feature of the circuit in FIG. 8B, one achieves the monophasic waveform of FIG. 8C, which is more nearly ideal than the prior art waveform of FIG. 3, and yet uses less total capacitance. This is especially important because the volume of the capacitor in a prior art implantable defibrillator is greater than that of any other component.

By using more than two capacitors, one can clearly see that the principles just illustrated can be combined in a wide variety of ways, and that the resulting capacitor networks can deliver varied waveforms. Placing the FETs of the switching network under the rule of a control network permits a practitioner to adapt defibrillation to changing patient needs, or to further enlightenment concerning optimal waveforms.

It is further possible to carry out non-invasive digital programming of the control network by programming means that have been developed for implanted-pacemaker programming. One prominent method uses digitally encoded RF electromagnetic radiation projected through the skirt and into the implanted electronic system. A telemetry repeater further improves the use convenience of this kind of system in the operating theater.

Since a defibrillator system typically requires that several amperes and hundreds of volts be delivered to the heart muscle, the power requirements are unusual by the standard of ordinary implanted electronic systems. Because the pulses are of brief duration, fortunately, the energy requirements are brought within tractable limits. Nonetheless, the energy that must be implanted in battery form is significant, especially as duty cycle increases, and is a foremost consideration in the engineering and application of this kind of system.

Some implanted electronic systems are able to operate at extremely low voltages. In defibrillation, however, several hundred volts are required. While the needed high voltages can be derived from low voltage dc sources through "chopping" techniques, the task is simplified if the dc source has higher voltage. One way to obtain high dc voltage is with a series-array photovoltaic device. Monolithic versions are particularly attractive for reasons of reliability, efficiency, and small size. These can be implanted subcutaneously and can be activated by an external light source aimed at the area of implantation. Higher light-transmission efficiency can be achieved, though admittedly with serious area limitations, by using the body's natural "windows", the fingernails. Various modifications can be made to the present invention without departing from the apparent scope hereof.

We claim:

1. An improved implantable defibrillator system for producing a capacitive-discharge electrical countershock, the implantable defibrillator system being a self-contained human implantable device including a capacitor means for storing an electrical charge, means for internally charging the capacitor means, means for sensing a cardiac dysrhythmia in a human patient and means for selectively discharging the electrical charge as an electrical countershock to be delivered through at least two implantable discharge electrodes in response to the means for sensing the cardiac dysrhythmia, the improvement comprising:

the capacitor means including at least two separate capacitor units, each capacitor unit having a separately electrically accessible anode output and a separately electrically accessible cathode output; and the means for selectively discharging the electrical charge including electronic switching circuitry means electrically connected between at least one output of each capacitor unit and electrically connected between at least one output of each capacitor unit and each of the at least two implantable discharge electrodes for selectively electrically connecting the anode output and the cathode output of the at least two capacitor units to the at least two implantable discharge electrodes to independently establish both a topology and a polarity for the electrical countershock during a discharge period of time when the electrical charge is discharged such that the topology is selectable from the group consisting of a parallel configuration of the capacitor units, a series configuration of the capacitor units, a sequential configuration of the capacitor units, or any combination thereof.

2. The implantable defibrillator system of claim 1 in which the electronic switching circuitry means selectively changes the polarity of the electrical countershock once to produce an initial portion and a succeeding portion of a biphasic waveform.

3. The implantable defibrillator system of claim 2 in which the electronic switching circuitry means changes the topology during the initial portion of the biphasic waveform.

4. The implantable defibrillator system of claim 2 in which the electronic switching circuitry means changes the topology during the succeeding portion of the biphasic waveform.

5. The implantable defibrillator system of claim 1 in which the electronic switching circuitry means selectively discharges in sequence at least a portion of the electrical charge stored by the at least two capacitor units.

6. The implantable defibrillator system of claim 5 in which the electronic switching circuitry means selectively changes the topology after the portion of the electrical charge is discharged in sequence and then selectively discharges at least a second portion of the electrical charge stored by at least one of the at least two capacitor units.

7. The implantable defibrillator system of claim 1 in which there are two capacitor units, each of which is comprised of a pair of electrolytic capacitors electrically connected in series.

\* \* \* \* \*